United States Patent [19]

Kawahara et al.

[11] Patent Number: 4,652,593
[45] Date of Patent: Mar. 24, 1987

[54] DENTAL ALUMINATE CEMENT COMPOSITIONS

[75] Inventors: Haruyuki Kawahara, No. 28, Tokocho 1-chome, Moriguchi-shi, Osaka-fu; Shoji Takeda, Ibaraki; Hiroshi Oshima, Sakai; Kentaro Tomioka, Chofu; Shoji Akahane, Higashikurume; Eiichi Yoshii; Kazuo Hirota, both of Tokyo, all of Japan

[73] Assignees: G-C Dental Industrial Corp., Tokyo; Haruyuki Kawahara, Moriguchi, both of Japan

[21] Appl. No.: 828,706

[22] Filed: Feb. 12, 1986

[30] Foreign Application Priority Data

Apr. 5, 1985 [JP] Japan ................................ 60-71063

[51] Int. Cl.$^4$ .............................................. A61K 5/01
[52] U.S. Cl. ..................................... 523/116; 106/35; 433/228.1; 523/117
[58] Field of Search ................... 523/116, 117; 106/35; 433/228.1

[56] References Cited

U.S. PATENT DOCUMENTS 4,542,167  9/1985  Aoki .................................... 523/109
4,591,384  5/1986  Akahane et al. .................... 523/116

Primary Examiner—Lorenzo B. Hayes
Attorney, Agent, or Firm—Oblon, Fisher, Spivak, McClelland & Maier

[57] ABSTRACT

A dental cement composition consisting of a composition A and a composition B, said composition A comprising (a) 100 parts by weight of a powder containing 20 to 70% by weight of calcium oxide and 30 to less than 80% by weight of aluminum oxide, said powder being coated on the surface with a water-soluble high-molecular substance, and (b) 2 to 70 parts by weight of a calcium hydroxide powder, and said composition B comprising an aqueous solution containing 0.01 to 70% by weight of a water-soluble high-molecular substance.

4 Claims, No Drawings

DENTAL ALUMINATE CEMENT COMPOSITIONS

FIELD OF THE INVENTION

The present invention relates to a dental aluminate cement composition and, particularly, to a dental composition best-suited for pulp capping, lining, base and root canal filling. More specifically, the present invention is concerned with a dental aluminate cement composition consisting of a composition A and a composition B, said composition A comprising (a) 100 parts by weight of a powder containing more than 20 to 70% by weight of calcium oxide and 30 to less than 80% by weight of aluminium oxide, said powder being coated on the surface with a water-soluble high-molecular substance, and (b) 2 to 70 parts by weight of a calcium hydroxide powder, and said composition B comprising an aqueous solution containing 0.01 to 70% by weight of a water-soluble high-molecular substance.

BACKGROUND OF THE INVENTION

Dental cements are material used currently in a wider range of dental fields. For instance, they are used as setting for prosthetic appliances and orthodontic appliances, filling for restoration of caries cavity, lining, base, pulp capping, build up, root canal filling, etc. Out of the dental cements, zinc phosphate cement, polycarboxylate cement, glass ionomer cement, etc. have relatively excellent physical properties. However, these cements set because of reaction between acids and bases. Since acids are used in these systems, they cannot be used in the vicinity of the alive dental pulp due to the irritating action of the acids. At present, zinc oxide eugenol cement, calcium hydroxide, etc. are used as the pulp capping material at regions adjacent to the dental pulp. In particular, the calcium hydroxide cement is used as the direct pulp capping material. Since these cements are expected to show a pharmaceutical effect, they can be used as the pulp capping material without anxiety to some degrees. However, there is a problem, since they possess physical properties such as low crushing strength and high solubility, which are insufficient for the base material. Where the calcium hydroxide cement is used as the lining material in, for instance, a very deep cavity, it is required to prepare the so-called "cement base" with glass ionomer cement, zinc phosphate cement and polycarboxylate cement, each having a relatively high crushing strength, due to the low strength thereof, thus resulting in complicated manipulation. Typical calcium hydroxide is prepared by cross-linking of calcium hydroxide with salicylic acid ester. Although this product has a low strength, it shows a certain hardening property. However, this product takes on the paste form showing so strong a hydrohobic property that it is lacking in the affinity with respect to teeth. For that reason, there is a problem in connection with the interface thereof with respect to teeth.

SUMMARY OF THE INVENTION

In coseqeunce of intensive and extensive studies made of the pulp capping cement offering such problems, it has been found that such problems are inexpectedly solved by a dental cement composition consisting of a composition A and a composition B, said composition A comprising (a) 100 parts by weight of a powder containing 20 to 70% by weight of calcium oxide and 30 to less than 80% by weight of aluminium oxide, said powder being coated on the surface with a water-soluble high-molecular substance, and (b) 2 to 70 parts by weight of a calcium hydroxide powder, and said composition B comprising an aqueous solution containing 0.01 to 70% by weight of a water-soluble high-molecular substance.

DETAILED EXPLANATION OF THE PREFERRED EMBODIMENTS OF THE INVENTION

The composition of the present invention shows a much higher crushing strength and a lower solubility, as compared with the conventional calcium hydroxide cement used as the pulp capping and the lining material. Due to its particularly high crushing strength, the composition of the present invention allows pulp capping, lining and base to be applied with the same material, and makes manipulation so easy that a period of time required for treatment is curtailed. A mixed paste sludge obtained from the composition of the present invention has also an appropriate flowability, and excels in the manipulation property. Furthermore, the hydrophilic property of the invented composition gives rise to another advantage that it adheres closely to dentine due to its very excellent affinity thereto. At the same time, the composition of the present invention offers a further advantage that it shows a very good preservability in spite of the fact that the powder is basic. Still further, the powder coated with a water-soluble high-molecular substance can extend a manipulation period of time without delaying the initial setting or hardening, and can thus introduce improvements into the hardening property.

On the other hand, the composition of the present invention further containing an X-ray contrast medium is useful for postoperative diagnosis, and is clinically very effective. The "powder containing more than 20% by weight to 70% by weight of calcium oxide and 30% by weight to less than 80% by weight of aluminium oxide and coated on the surface with a water-soluble high-molecualr substance" may be prepared in various processes. For instance, a calcium-containing substance such as calcium carbonate, calcium hydroxide or calcium oxide is permitted to react with an aluminium-containing substance such as aluminium hydroxide, aluminium oxide or aluminium carbonate at high temperatures. After sintering or melting, the reaction product is cooled and pulverized into a powder which is, in turn, coated with a water-soluble high-molecular substance. In this process, the powder as defined in the foregoing is obtained. Sintering or melting may be conducted according to the process known in the art and, optionally, with the use of a suitable amount of aids. Depending upon the conditions applied, the calcium and aluminium in said powder form calcium aluminate compounds such as $3CaO.Al_2O_3$, $12CaO.7Al_2O_3$, $CaO.Al_2O_3$, $CaO.2Al_2O_3$, $CaO.6Al_2O_3$, etc. in addition to CaO and $Al_2O_3$. It is to be understood that suitable amounts of other oxides, fluorides, chlorides, sulfates, phosphates, carbonates and the like may be added with no difficulty during sintering or melting. The additives applied may include oxides such as strontium oxide, magnesium oxide, silicon dioxide, iron oxide (II) or yttrium oxide as well as fluorides, chlorides, sulfates and phospates of calcium, strontium, sodium, potassium and aluminium. In other words, no particular limitations are imposed to that powder, except that it contains more than 20% by weight to 70% by weight of calcium oxide and 30% by weight to less than 80% by weight of aluminium oxide. The proportion of calcium oxide in said powder is preferably in a range of more than 20% by weight to 70% by weight based on the total weight thereof. Particular preference is given to a range of 25% by weight to 50% by weight. When the amount of calcium oxide is less than 20%, the hardening reaction proceeds too slowly. When that amount exceeds 70%, on the other hand, the hardening of cement paste is too rapid to curtail a time period allowed for manipulation to an extreme extent and, at the same time, to lower the strength thereof. The proportion of aluminium oxide in said powder is preferably in a range of 30% by weight to less than 80% by weight based on the total weight thereof, but particular preference is given to a range of 50% by weight to 75% by weight. When the amount of aluminium oxide is less than 30%, there is a drop of the strength of the hardened cement product. When that amount exceeds 80% by weight, on the other hand, the hardening reaction of mixed cement paste becomes too slow and unpractical. Although the powder sintered at such a high temperature can be used as such to obtain a tough hardened product, yet it is easily affected by atmospheric moisture and carbon dioxide due to the strong basicity of that powder. Thus, there is a problem in connection with the preservation of that powder over a long period. In accordance with the present invention, the coating of the surface of the powder with a water-soluble high-molecular substance makes a great contribution to improvements in preservability. The coating of the surface of the powder with a water-soluble high-molecular substance also makes a contribution to improvements in the hardening property. In other words, it is possible to extend a manipulation period of time without delaying the initial setting time. Such water-soluble high-molecular substances may include polyacrylic acid, sodium polyacrylate, polyethylene imine, polyvinyl alcohol, polyethylene glycol, polyethylene oxide, polyvinyl pyrrolidone, carboxymethyl cellulose, methyl cellulose, hydroxyethyl cellulose, hydroxypropyl cellulose, cellulose acetate phthalate, sodium (or potassium) alginate, gum arabic, etc. Out of these, preference is given to polyvinyl pyrrolidone, sodium polyacrylate and hydroxypropyl cellulose. These water-soluble high-molecular substances may be deposited on the surface of the powder in the conventional process. For instance, such a substance may be incorporated in a ball mill while, at the same time, the powder is pulverized therein, for the deposition thereof onto the surface of the powder. Alternatively, such a substance may be melted or suspended in a solvent such as an alcohol, acetone or water, and the resulting solution is mixed with a pulverulent body containing calcium aluminate, followed by removal of the solvent by means of drying, etc. The calcium hydroxide power and X-ray contrast medium contained in the composition A may partly or wholly be coated with the water-soluble high-molecular substance. It is then possible to coat the calcium hydroxide powder and the X-ray contrast medium with the water-soluble high-molecular substance together with or independently of the powder containing calcium aluminate. The water-soluble high-molecular substance used for coating may have a molecular weight of 1,000 to 1,000,000; however, a preferred molecular weight is in a range of 1,000 to 100,000. Too large a molecular weight gives rise to a disadvantage that the powder cannot uniformly be coated. Too low a molecular weight causes another disadvantage that, unless a large amount of coating is applied, no prominent effect is brought about, so that the physical properties such as crushing strength deteriorate. Sufficiently, the proportion of the water-soluble high-molecular substance used may ususally be no higher than 5% by weight based on the total weight of the pulverulent body to be coated, but preference is given to a range of 0.05 to 2% by weight.

No critical limitation is imposed upon the X-ray contrast media used in the present invention. However, since the larger the atomic number, the higher the degree of the X-ray absorption, use is usually made of a substance having a relatively large atomic number and of low toxicity. For example, use may be made of metal powders, alloy powders, oxides such as yttrium oxide and zinc oxides, salts such as barium sulfate, calcium tungstate and bismuth oxycarbonate, sodium iodide, iodoform, etc. Usually, these X-ray contrast media are contained in the composition A for use, since they are often insoluble in water. In some cases, however, they may be incorporated into the composition B. Whether water-soluble or water-insoluble, they may be suspended in the composition B for use. Optionally, the X-ray contrast media may be blended with the "powder containing more than 20 to 70% by weight of calcium oxide and 30 to less than 80% by weight of aluminium oxide", when it is prepared by sintering or melting, followed by sintering or melting. In this case, the contrasting properties are afforded to the "powder containing more than 20 to 70% by weight of calcium oxide and 30 to less than 80% by weight of aluminium oxide" per se.

The compositions of the present invention, free from any X-ray constrast medium, are also usable in view of the physical properties. Rather, the physical properties of the hardened cement are by no means lower in the presence of X-ray contrast media than in the absence thereof. However, when dentists use the compositions of the present invention for the actually clinical purpose, i.e. for pulp capping, lining, base or root canal filling, the provision of the contrasting properties to the material helps postoperative diagnosis, and is one of the requirements that said material should have. Preferably, the X-ray contrast media are present in the compositions of the present invention in an amount of 10 to 50% by weight relative to the overall weight thereof. In an amount of less than 10%, there is a reduced or limited contrasting effect, whereas in an amount exceeding 50%, there is a drop of physical properties. Usually, a range of 10 to 40% by weight is preferred. It is to be understood that the compositions of the present invention can also be applied as the root canal filling material due to their good affinity to living tissues; however, they may contain 50% or more of the contrast medium owing to the need of having high crushing strength.

No critical limitation is imposed upon the size of the calcium hydroxide powder used. Usually, however, that powder preferably passes through a 80-mesh seive, more preferably a 120-mesh sieve. Calcium hydroxide has a pharmaceutical effect, and is said to promote the growth of secondary dentin. When it is used with the pulp capping material in the present invention, similar effects are expected. The incorporation of calcium hydroxide also results in improvements in the crushing strength of the hardened cement mass. It is preferred that the amount of calcium hydroxide contained in the composition A is 2 to 70 parts by weight per 100 parts by weight of the "powder containing more than 20 to 70% by weight of calcium oxide and 30 to less than 80% by weight of aluminium oxide, and coated on the surface with a water-soluble high-molecular substance". In an amount of less than 2 parts by weight, the calcium hydroxide does not produce its own effect, whereas in an amount exceeding 70 parts by weight, there is a delay in the solidification or hardening time with the resulting drop of crushing strength.

The composition A in the composition of the present invention has hydraulic properties, and form a hardened mass upon mixed with water. Thus, it is possible to satisfactorily use the composition of the present invention even only by mixing with water. It is to be noted, however, that the strength of the hardened mass is enhanced by the incoporation of a water-soluble high-molecular substance into the composition B. In particular, improvements are introduced into tensile strength. In addition, a delay in the hardening time results in an extension in the time allowed for manipulation. As is the case with the water-soluble high-molecular substance for coating the composition A, various water-soluble high-molecular substances may be used for the composition B. Among others, polyvinyl pyrrolidone, polyethylene oxide, sodium polyacrylate and sodium polymethacrylate are particularly preferred. The molecular weight of the water-soluble high-molecular substance used is in a range of, preferably 1,000 to 1,000,000, more preferably 1,000 to 100,000. Too large a molecular weight inhibits the hydration and hardening reactions between the water-soluble high-molecular substance and the cement powder, makes the initial hardening properties unpreferred so that hardening reaction become slow, and incurs a substantial drop of strength. A molecular weight of less than 1000 makes no contribution to any improvements in crushing strength. The proportion of the water-soluble high-molecular substance contained in the composition B may properly be selected from the range of 0.01 to 70% by weight depending upon the molecular weight thereof.

The viscosity of the composition B is preferably in a range of 5 to 5,000 cP. However, a more preferable range of viscosity is 10 to 2,000 cP.

No special limitation is placed upon the powder/liquid ratio of the composition A/B. Although it may be selected depending upon the clinical purpose, the composition A may usually be used in an amount of 1.5 to 5.0 grams per 1 gram of the composition B.

The present invention will now be explained concretely with reference to the following non-restricitive examples.

EXAMPLE 1

Two hundred (200) grams of aluminium hydroxide and 100 grams of calcium carbonate were well mixed together in a porcelain mortar, and the resulting mixture was charged in a platinum crucible, and sintered at 1350° C. for 12 hours in an electric furnace. After sintering, the sintered body was cooled off in the air, pulverized for 2 hours in a ball mill, and screened out through a 120-mesh sieve to obtain a calcium aluminate powder. One hundred (100) grams of said powder were well blended with 20 grams of the highest grade reagent calcium hydroxide. Thereafter, 20 grams of a 3% ethanol solution of polyvinyl pyrrolidone (M.W. 40,000) were slowly added dropwise to the resulting mixture, while it was further mixed. The powder wetted with the ethanol solution was spread over an evaporating dish, and was dried at 110° C. for 2 hours in a steam drier. In this process, a composition A was prepared.

On the other hand, a 10% aqueous solution of polyvinyl pyrrolidone (M.W. 40,000) was prepared as a composition B.

The thus obtained composition A and B were mixed together for 30 seconds in a proportion of 2.0 grams to 1.0 gram. That is, the powder (composition A) was divided into two portions. After one portion had been mixed with the aqueous solution of the composition B for 15 seconds, another portion was added to the resulting mix for further 15 second-mixing. A total of mixing time thus amounted to 30 seconds. According to JIS T 6602 specificated on the dental zinc phosphate cement, the thus obtained cement was measured on the consistency one minute after the initiation of mixing in a constant temperature room of a temperature of 23.0°±0.2° C. and a humidity of 50±2%, the initial setting time and the crushing strength after one day. As a result, that cement was found to have a consistency of 28 mm, an initial setting time of just 4 minutes and a crushing strength after one day of 710±40 kg/cm$^2$. This suggests that the cement of this example is excellent as the cement for pulp capping, lining, and base.

EXAMPLE 2

In the process similar to that of Example 1, a calcium aluminate powder was prepared, which passed through a 120-mesh sieve. Apart from this, 5 grams of hydroxypropylmethyl cellulose were dissolved in 100 cc of a mixed solvent of 50% methanol and 50% methylene chloride. While well mixing 100 grams of the calcium aluminate powder, 20 grams of the resulting solution were slowly added dropwise thereto for surface treatment. The thus surface-treated calcium aluminate powder was dried at 110° C. for 2 hours in a steam drier. After drying, 100 grams of said powder were well mixed with 25 grams of calcium hydroxide to prepare a A. A composition B was prepared in the process identical with that of Example 1.

The compositions A and B were mixed together in a proportion of 2.0 grams to 1.0 gram and in the same manner as in Example 1. Referring to the physical properties, the resulting cement was found to have a consistency of 41 mm, a crushing strength of 680±30 kg/cm$^2$ and initial setting time of 4 minutes 15 seconds. This suggests that the cement of this example is more excellent for pulp capping, lining and base than ever before.

EXAMPLE 3

One hundred (100) grams of aluminium hydroxide were well mixed with 77 grams of calcium carbonate in a porcelain mortar, and the resulting mixture was charged in a platinum crucible, and sintered at 1,400° C. for 10 hours in an electric furnace. After sintering, the sintered product was cooled off in the air, pulverized in a mortar, and screened out through a 150-mesh sieve to prepare a sample. Three (3) grams of polyvinyl pyrrolidone (M.W. 40,000) were completely dissolved in 97 grams of methanol with stirring. Ten (10) grams of a methanol solution of polyvinyl pyrrolidone were slowly added dropwise to 50 grams of said powder, while mixed amply in a mortar. The powder wetted with the alochol solution was spread over an evaporating dish, and was dried at 110° C. for 2 hours in a steam drier to evaporate off the methanol. Fifteen (15) grams of the highest grade reagent barium sulfate and 5 grams of the highest grade reagent calcium hydroxide were completely blended with 30 grams of the thus obtained powder to prepare a composition A. On the other hand, 8 grams of sodium polyacrylate (M.W. 20,000) were dissolved in 92 grams of pure water to prepare a composition B. The thus obtained compositions A and B were mixed together in a proportion of 2.5 grams to 1.0 gram. Mixing and measurement were effected in the process identical with that of Example 1. As a result, the obtained cement was found to have physical properties represented in terms of an initial setting time of 3 minutes 30 seconds, a consistency of 40 mm and a crushing strength of 620±15 kg/cm$^2$. This suggests that the cement of this example is the most excellent pulp capping, lining and base cement ever.

EXAMPLE 4

In Example 3, 100 grams of aluminium oxide was used in place of 100 grams of aluminium hydroxide to prepare a sample according to Example 1. The physical properties of that sample were measured. The obtained sample was found to have a consistency of 38 mm, an initial setting time of 4.0 minutes and a crushing strength of 650±25 kg/cm$^2$. This suggests that the cement of this example is the most excellent pulp capping, lining and base cement ever.

EXAMPLES 5 AND 6

In Examples 3 and 4, 3 grams of polyvinyl pyrrolidone (M.W. 40,000) were dissolved in 97 grams of methanol. In these examples, 5 grams of hydroxypropyl cellulose (M.W. 40,000) were dissolved in 95 grams of ethanol to prepare samples according to Example 1, which were found to show the following initial setting time and crushing strength.

|  | Initial setting Time | Crushing Strength |
| --- | --- | --- |
| Example 5 | 3 min. 30 sec. | 625 ± 15 kg/cm$^2$ |
| Example 6 | 4 min. 00 sec. | 660 ± 20 kg/cm$^2$ |

EXAMPLES 7 TO 9

The amount of calcium carbonate was 77 grams in Example 3, but it was varied in these examples, say, 30 grams, 50 grams and 113 grams. Samples were prepared in the process identical with that of Example 1, and were found to have the following physical properties.

|  | Initial setting Time | Crushing Strength |
| --- | --- | --- |
| Example 7 | 4 min. 30 sec. | 670 ± 30 kg/cm$^2$ |
| Example 8 | 4 min. 00 sec. | 650 ± 30 kg/cm$^2$ |
| Example 9 | 3 min. 00 sec. | 600 ± 25 kg/cm$^2$ |

EXAMPLES 10 TO 12

In Example 3, the composition B was prepared by dissolving 8 grams of sodium polyacrylate (M.W.: 20,000) in 92 grams of pure water. In these examples, however, the following modification was made to the composition B.

| Example 10: | Sodium Polyacrylate (M.W.: 7,000) | 15 grams |
| --- | --- | --- |
|  | Pure Water | 85 grams |
| Example 11: | Sodium Polyacrylate (M.W.: 7,000) | 10 grams |
|  | Sodium Polyacrylate (M.W.: 1000,000) | 1 gram |
|  | Pure Water | 89 grams |
| Example 12: | Sodium Polyacrylate (M.W.: 50,000) | 1 gram |
|  | Sodium Polyacrylate (M.W.: 70,000) | 2 gram |
|  | Pure Water | 97 grams |

The physical properties of the mixed products obtained by using the same composition A and these compositions B were measured. The results are as follows.

|  | Initial setting Time | Crushing Strength |
| --- | --- | --- |
| Example 10 | 3 min. 30 sec. | 640 ± 15 kg/cm$^2$ |
| Example 11 | 4 min. 00 sec. | 670 ± 30 kg/cm$^2$ |
| Example 12 | 4 min. 00 sec. | 610 ± 20 kg/cm$^2$ |

EXAMPLE 13

One hundred (100) grams of aluminium oxide and 80 grams of calcium carbonate were well blended together in a porcelain mortar, and the resulting mixture was charged in a platinum crucible, which was in turn placed in an electric furnace for 2 hours for calcination. After pulverization, the pulverized body was sintered for 5 hours in an electric furnace maintained at 1300° C. After sintering, the sintered product was cooled off in the air, re-pulverized in a mortar and passed through a 150-mesh sieve to prepare a sample. While stirring, 3 grams of hydroxypropyl cellulose (M.W.: 40,000) were entirely dissolved in 97 grams of ethanol. Ten (10) gram ethanol solution of hydroxypropyl cellulose were added dropwise to 50 grams of the aforesaid cement powder in a mortar, while sufficient stirring was effected. On the other hand, 12 grams of the same ethanol solution of hydroxypropyl cellulose were well blended with 50 grams of calcium hydroxide powder. The cement and calcium hydroxide powders wetted with the alcohol were separately spread over evaporating dishes, and were dried in a steam drier at 110° C. for 2 hours for complete evaporation of ethanol. Ten (10) grams and 65 grams of the thus obtained calcium hydroxide and cement powder were further well blended with 25 grams of barium sulfate to prepare a composition A. On the other hand, 10 grams of sodium polyacrylate (M.W.: 15,000) were dissolved in 90 grams of water to prepare a composition B. The thus obtained compositions A and B were mixed together in a proportion of A to B of 3 to 1 gram. Initial setting time and crushing strength were measured according to Example 1. Initial setting time: 3 min. 30 sec. Crushing strength: 690±30 kg/cm$^2$.

EXAMPLE 14

Barium sulfate was also treated with the ethanol solution of hydroxypropyl cellulose of Example 13. That is, 10 grams of the ethanol solution were slowly added to 50 grams of barium sulfate, followed by well mixing. Thereafter, the mixed product was dried at 110° C. for 2 hours in a steam dirier for complete evaporation of ethanol. With respect to the remaining procedures, Example 13 was repeated to prepare a sample, the physical properties of which were measured. The thus obtained compositions A and B were mixed together in a proportion of A to B of 3.2 to 1.0 gram. Initial setting time: 3 min. 30 sec. Crushing strength: 680±30 kg/cm$^2$.

From the foregoing, it has been found that the products according to the examples are the most excellent pulp capping, lining and base cements ever.

COMPARISON EXAMPLE 1

The physical properties of calcium hydroxide cement (of the paste type) which is manufactured by C Co. Ltd., and is widely used as the pulp capping and the lining cement were measured. One (1.00) gram of a catalyst was mixed with 1.17 grams of the paste. Initial setting Time: 3 min. 30 sec. Crushing strength: $152\pm7$ kg/cm$^2$.

COMPARISON EXAMPLE 2

The cement powder not coated on the surface with polyvinyl pirrolidone was used in place of the cement powder coated on the surface with polyvinyl pirrolidone in Example 3 and other procedures were the same as in Example 1 to prepare a sample. Both compositions A of Example 3 and Comparison Example 2 were exposed to the air to measure the initial setting time after two weeks. The composition of Comparison Example 2 was delayed by about two minutes, but the composition of Example 1 was identical in the solidification tiem.

|  | Initial setting Time | Initial setting Time After Two Weeks |
|---|---|---|
| Example 1 | 3 min. 30 sec. | 3 min. 30 sec. |
| Comparison Example 2 | 3 min. 30 sec. | 5 min. 30 sec. |

COMPARISON EXAMPLE 3

Two hundred (200) grams of aluminium hydroxide and 10 grams of calcium carbonate were well blended together in a porcelain mortar, and the resulting mixture was placed in a platinum crucible, which was then placed in an electric furnace of 1300° C. for 12 hour-sintering. After sintering, the sintered body was cooled in the air, and was pulverized for 2 hours in a ball mill. The resulting powders were passed through a 120-mesh sieve to obtain calcium aluminate powders. Ten (10) grams of calcium hydroxide were well blended with 100 grams of said powders to form a composition A.

Two (2.0) grams of the composition A were mixed with 1.0 gram of distilled water to measure the initial setting time and crushing strength after one day. Initial setting time: 10 min. 30 sec. Crushing strength after one day: $240\pm15$ kg/cm$^2$.

The pulp capping, lining and base cements obtained according to Examples 1 to 15 of the present invention are more excellent than those of Comparison Examples 1 to 3.

We claim:

1. A dental cement composition consisting of a composition A and a composition B, said composition A comprising (a) 100 parts by weight of a powder containing more than 20 to 70% by weight of calcium oxide and 30 to less than 80% by weight of aluminium oxide, said powder being coated on the surface with a water-soluble high-molecular substance, and (b) 2 to 70 parts by weight of a calcium hydroxide powder, and said composition B comprising an aqueous solution containing 0.01 to 70% by weight of a water-soluble high-molecular substance.

2. A dental cement composition as defined in claim 1, in which said comosition A and/or B contain an X-ray contrast medium.

3. A dental cement composition as defined in claim 1 or 2, in which an aqueous solution containing said water-soluble high-molecular substance in said composition B has a viscosity of 5 to 5,000 cP.

4. A dental cement composition as defined in any one of claims 1 to 3, in which such water-soluble high-molecular substance in said composition B is at least one selected from the group consisting of polyvinyl pyrrolidone, polyethylene oxide, sodium polyacrylate and sodium polymethacrylate.

* * * * *

UNITED STATES PATENT AND TRADEMARK OFFICE
CERTIFICATE OF CORRECTION

PATENT NO. : 4,652,593

DATED : March 24, 1987

INVENTOR(S) : HARUYUKI KAWAHARA, ET AL

It is certified that error appears in the above-identified patent and that said Letters Patent is hereby corrected as shown below:

<u>Col.</u>  <u>Line</u>

9     32,  delete "10" and insert --100--.

Signed and Sealed this

Twentieth Day of September, 1988

Attest:

DONALD J. QUIGG

Attesting Officer          Commissioner of Patents and Trademarks